United States Patent [19]

Schaller et al.

[11] Patent Number: 5,368,545
[45] Date of Patent: Nov. 29, 1994

[54] ACCESSORY DEVICE FOR LAPAROSCOPIC OPERATIONS

[75] Inventors: Günter Schaller, Freiburg; Dietmar Klietsch, Waiblingen, both of Germany

[73] Assignee: Willy Rusch AG, Kernen i.R., Germany

[21] Appl. No.: 983,506

[22] Filed: Nov. 30, 1992

[30] Foreign Application Priority Data

Dec. 5, 1991 [DE] Germany ............................. 4140156

[51] Int. Cl.⁵ ............................................. A61F 13/00
[52] U.S. Cl. ...................................... 600/37; 128/846; 128/849; 128/850; 128/851; 128/855; 128/856
[58] Field of Search ....................... 128/760, 767–769, 128/896, 849–852, 855–856; 600/37; 604/332, 337–339, 341–344

[56] References Cited

U.S. PATENT DOCUMENTS

| | | |
|---|---|---|
| 3,435,821 | 4/1969 | Bennett. |
| 3,736,934 | 6/1973 | Hennessy ............................ 604/342 |
| 4,899,762 | 2/1990 | Muller ................................. 128/850 |
| 4,917,694 | 4/1990 | Jessup ................................. 604/362 |
| 5,037,379 | 8/1991 | Clayman et al. .................... 128/850 |
| 5,209,744 | 5/1993 | Abe et al. ........................... 604/338 |

OTHER PUBLICATIONS

"Complete Evisceration of Small Bowel" Davis Rubber Co. catalogue, 1959.
Journal of Urology, vol. 146 (1991), pp. 278–282, Clayman et al. "Laparoscopic Nephrectomy: Initial Case Report".

Primary Examiner—Jerome L. Kruter
Assistant Examiner—P. Zuttarelli
Attorney, Agent, or Firm—Fields, Lewis, Pittenger & Rost

[57] ABSTRACT

Accessory devices for laparoscopic operations can be combined with a plastic receptacle 2 in such a way that an opening formed outside the abdominal wall in a cover sheet 10 can be coupled in sealing relationship with an end of the plastic receptacle 2 that can be closed or opened. The plastic receptacle 2 is in this case still located inside the abdominal space, at least in part, the opening of the plastic receptacle 2 projecting beyond the abdominal wall 4.

11 Claims, 4 Drawing Sheets

ACCESSORY DEVICE FOR LAPAROSCOPIC OPERATIONS

BACKGROUND OF THE INVENTION

The invention relates to accessory devices for laparoscopic operations for use in combination with a plastic receptacle serving to receive tissue fragments that are to be removed by laparoscopic means, for intra-abdominal protected intermediate storage.

Connection elements for devices of this kind have been known from the publication Laparoscopic Nephrectomy: Initial Case Report, The Journal of Urology, Vol. 146, 278-282 August 1991.

In the case of laparoscopic operations performed through small openings in the abdominal wall, the extraction of organs, parts of an organ or of calculi may be difficult or even impossible without additional measures, and may be connected with additional risks for the patient.

During the operation, removed, intact, non-infective organ tissue usually is stored in the free abdominal space. This is, however, connected with the risk that the tissue may not be found again later. If intra-abdominal transmission of terms, or loss of organ fragments or calculi is to be feared, one must proceed to the extraction immediately, and this may complicate the operation or considerably extend its duration.

A suitable plastic receptacle placed inside the abdominal space may serve to receive the removed contaminated tissue fragments in the manner of an intermediate storage in order to avoid the before-mentioned disadvantages.

Intact organ tissue usually is removed through the umbilical incision. This presents no problems when the tissue, after having been pulled into the trocar sleeve, can be removed together with the latter. In most of the cases, however, the trocar diameter is too small. If this in the case, the tissue is pulled through the unprotected abdominal wall and may contaminate the latter.

It is not rare that the pulling forces exerted upon the tissue during extraction cause destruction of parts of the tissue, and during this process infective materials, tissue particles, malign cell formations or calculi may get into the free abdominal space.

Inflammatory, swollen organ tissue or big calculi, and their summation effects, may render the extraction impossible mechanically.

Consequently, techniques and instruments have been developed by means of which organ tissue can be disintegrated intra-abdominally, for example in the case of hysteromyoma. While mechanical and ultrasonic crushing of calculi can be employed in an intact gallbladder, their use in the free abdominal space, for crushing big calculi is not possible.

However, it is a necessity with all laparoscopic methods that tissue above a given maximum size must be reduced in size intra-abdominally by puncture, crushing, or mechanical destruction, before it can be extracted from the abdominal space because increasing the incision in the abdominal wall would be contrary to the very idea underlying the laparoscopic operation method. Crushing tissue intra-abdominally increases, however, the risk of infection in the abdominal space.

If an enlargement of the incision in the abdominal wall still becomes necessary during a laparoscopic operation, this is likewise in contradiction to the basic idea of least-invasive surgery, provides the risk of hemorrhage, of subsequent herniation, and requires the abdominal wall to be sutured by layers.

From the before-mentioned publication, a plastic pouch has been known in which the removed material can be crushed while still within the patient's body. One also developed a special crushing tool for this purpose.

The known plastic pouch and the instruments used in combination with it do not provide sufficient protection from the increased risk of contamination in laparoscopic operations inherent in this method. During removal and/or during intra-abdominal crushing of the tissue or calculi, infective or malign material may drip back into the abdominal wall and the abdominal space along the outside of the container.

There has been further known a big-caliber instrument by Kiaiber for extracting big calculi from the free abdominal space while preserving the pneumoperitoneum. However, this instrument also provides the risk that during removal of the tissue infective or malign material may drip back into the abdominal space from the trocar sleeve.

SUMMARY OF THE INVENTION

Now, it is the object of the present invention to provide accessory devices for a known plastic receptacle which make it possible to extract removed tissue from the abdominal wall either in toto or in fragmented form, without any risk of additional contamination, and to provide safe protection from additional contamination not only for the umbilical incision but also for the indirectly concerned incisions in the abdominal wall.

The invention achieves this object by the fact that an opening formed in a cover sheet outside of the abdominal wall can be coupled in sealing relationship with an end of the plastic receptacle that can be closed or opened.

The accessory devices according to the invention enable a cover sheet of sufficient size placed on the abdominal wall to be connected with the plastic receptacle in sealing relationship. In addition to the incision in the abdominal wall created by the umbilical trocar, all the other incisions required for the operation simultaneously can be protected from undesired contamination. Any liquid or malign cell formations escaping from the plastic receptacle in an uncontrolled manner are collected safely by the cover sheet, and any direct contact with the abdominal wall can be excluded. If special tools are used for extracting tissue fragments, either in toto or in fragmented form, from the plastic receptacle with the latter still partly in its intra-abdominal position, then the abdominal wall and the abdominal space are protected from direct contact with infective or malign tissue.

The plastic receptacle positioned in the abdominal space can be filled with the removed material, and can then be closed like a tobacco pouch. The plastic receptacle has a predefined tearing strength sufficient to stand even difficult extractions. Once the removed material or calculi have been placed in the plastic receptacle, the latter's content is stored provisionally in the abdominal space, without any risk of loss or transmission of germs.

According to a further development of the invention, the plastic receptacle is flexible and foldable, and comprises a shaft whose free end is enclosed by an opening formed in the cover sheet by an integrated ring, the free end and the ring being connectable by a closure element. Provided these conditions are fulfilled, the cover sheet can be connected with the plastic receptacle by closure elements of the most different shapes. Flange-like or tubular plugs may be inserted into the open end of the plastic receptacle, outside the abdominal wall, in which case the plug(s) is (are) locked in position on the ring of the cover sheet. The ring embraces the plastic receptacle in the area of its shaft. The free end of the plastic receptacle extends through the ring, and a portion of the shaft of the plastic receptacle can be fixed against displacement by the locking action of the connection elements between the ring and the closure element.

A particularly advantageous arrangement is obtained when the closure element is provided with a cylindrical section with notches, in particular an annular groove, formed on its outer circumferential surface, and when the section is provided with an opening and the ring is provided with means that can be brought into locking engagement with the notches. The ring may also be provided with additional noses designed for engaging recesses in the annular groove in form-locking relationship.

It is particularly advantageous in this case if the plastic receptacle is made from a transparent material. This provides the possibility not only to easily check the locking condition between the ring and the closure element, but also to extract removed material from the plastic receptacle under visual control.

If in the unfolded condition the plastic receptacle comprises a spherical section and a cylindrical section, it is suited for accepting both, the removed tissue and instruments which are introduced into the plastic receptacle through its opening. For the purpose of extraction, the umbilical trocar is removed, and the plastic receptacle is drawn immediately into the umbilical incision so as to seal the latter and to preserve the pneumoperitoneum. The spherical section of the plastic receptacle is placed completely in the abdominal space, while the cylindrical section of the plastic receptacle projects in part beyond the abdominal wall. One then places the ring of the cover sheet over the exposed section of the plastic receptacle and pushes the closure element into the latter whereby the closure element and the ring engage each other in locking relationship. As a result, the plastic receptacle is fixed against displacement. By producing a higher pressure in the plastic receptacle, as compared with the pneumoperitoneum, the plastic receptacle is unfolded inside the abdominal space. Any manipulations, such as crushing of removed material, can be carried out in this way easily in the plastic receptacle, under visual control from the outside.

For certain special applications it is also imaginable to arrange a plurality of separable plastic receptacles in one plastic receptacle. This enables the most different tissue formations to be stored separately inside the abdominal space, for subsequent recombination or separate examination.

If a cord of an easily distinguishable color, which marks the opening of the pouch, is integrated—in the form of a loop that can be pulled together—in that area of that end of the plastic receptacle which can be opened and closed, then this practical design provides a simple and particularly safe form of opening and closing the plastic receptacle.

The cover sheet is made from a material compatible with human skin, and exhibits a greater material thickness in the area of the opening than in the remaining areas of the sheet-like cover. The opening in the cover sheet is created, for example, by forming a ring from material of the cover sheet, or by inserting a ring into a hole in the cover sheet and uniting the materials of the two elements.

According to a particularly advantageous embodiment of the invention, the cylindrical section extends through the abdominal wall. The cylindrical section keeps the umbilical incision open, against the restoring forces of the abdominal wall, and when a hollow cylinder is introduced through the opening of the cylindrical section, in form-locking and sealing engagement, then it is also possible to irrigate the interior volume of the plastic receptacle while simultaneously introducing lithotripsy instruments into the interior of the plastic receptacle, provided the free end of the hollow cylinder is equipped with a sealable opening and a plurality of tubular connection pieces opening into the lumen of the hollow cylinder. If in this case the plastic receptacle is made from a transparent material, then lithotripsy can be carried out under visual control.

The tissue stored in the plastic receptacle can be crushed in a closed irrigatable space under intra-abdominal vision. Upon completion of the crushing process, the accessory devices can be removed and disposed of in toto. The accessory devices are suited especially for use in laparoscopic cholecystectomy.

Other advantages will become apparent from the description and the attached drawing. Also, the before-mentioned features and other features that will be described below can be used according to the invention each individually, or in any desired combination. The description of certain embodiments of the invention is not to be understood as comprehensive enumeration, but is given only by way of example.

BRIEF DESCRIPTION OF THE DRAWINGS

The invention will now be described in more detail with reference to the drawing in which.

DETAILED DESCRIPTION

Figure 1:
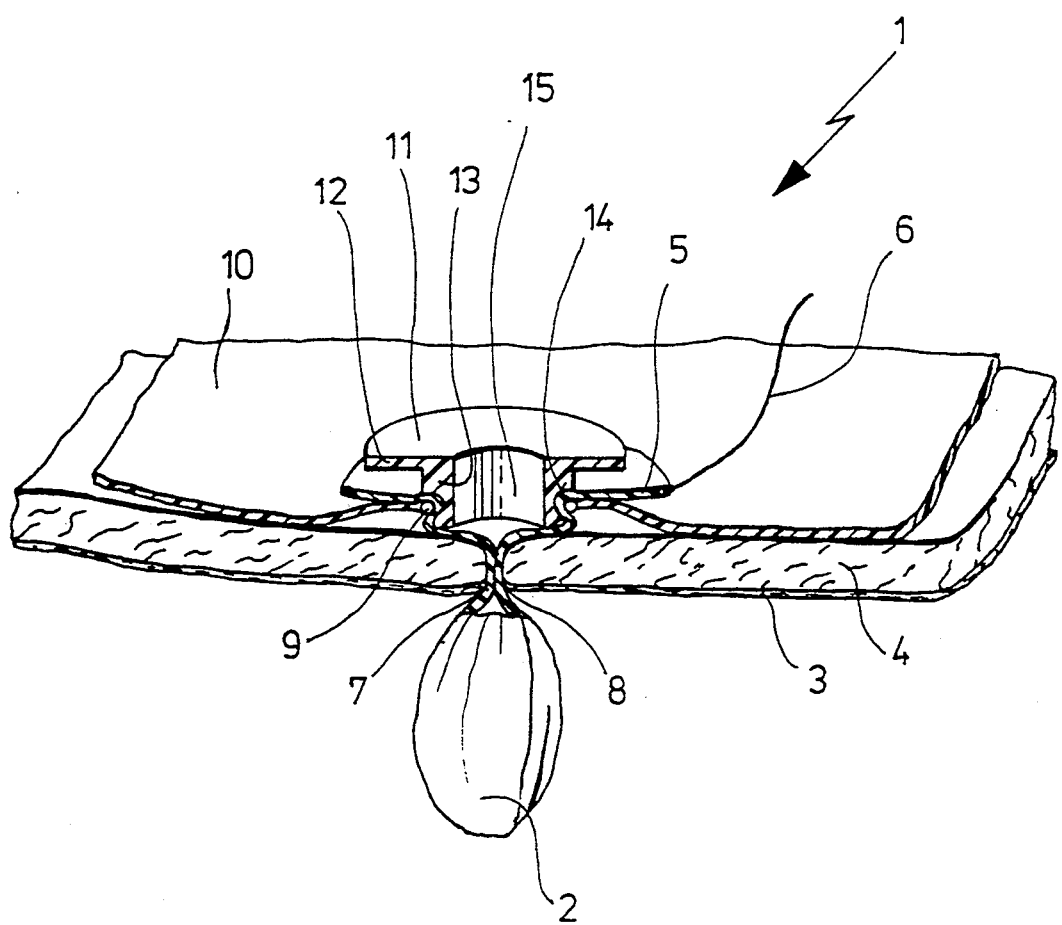
FIG. 1 shows a partly cross-sectional view of an accessory device according to the invention, with part of a plastic receptacle positioned inside an abdominal space.

The different figures of the drawing show, partly very diagrammatic, representations of the subject-matter of the invention and are not true to scale. The objects represented in the different figures are enlarged in part to give a clearer picture of their structure.

In FIG. 1, elements of the type used in laparoscopic operations are indicated by reference numeral 1. A plastic receptacle 2 extends in outward direction through the peritoneum 3 and the abdominal wall 4. In the area of the free end 5 of the plastic receptacle 2, a cord 6 is integrated in the form of a loop that can be pulled together. By pulling together the cora 6, it is possible to close the plastic receptacle 2 which consists of a robust and tear-resisting as well as flexible and foldable plastic film. When the cord 6 is loosened, the free end 6 of the plastic receptacle 2 can be opened. Natural restoring forces of the incision in the abdominal wall have the effect to tightly close the plastic receptacle illustrated by the figure. Outside the abdominal wall 4, a shaft 8 of the plastic receptacle 2 is fully enclosed by a ring 9 whose material is united with the material of a cover sheet 10. A closure element 11, formed as a single piece and consisting of an annular to disk-shaped section 12 and a cylindrical section 13, engages the plastic receptacle 2 by its cylindrical section 13. The ring 9 and the closure element 11 engage each other in locking relationship through an annular groove 14 formed on the outer surface of the cylindrical section 13. The contour of the ring 9 is adapted to the annular groove 14 in such a way that the shaft 8 of the plastic receptacle 2 can extend between the cylindrical section 13 and the ring 9, and the ring 9 yet can be in frictional and form-locking engagement with the groove 14. The closure element 11 is provided with an opening 15 which exhibits a circular cross-section in the example illustrated in FIG. 1. One end of the closure element 11 is in indirect contact with the skin, via the plastic receptacle 2. The restoring forces of the incision in the abdominal wall can be overcome by suitable instruments, for extracting from the plastic receptacle 2, the greatest part of which is located inside the abdominal space, any tissue or calculi that may be contained therein. The closure element 11 may also be arranged in such a way that its cylindrical section 13 extends through the abdominal wall 4 and the peritoneum 3. The locking engagement between the ring 9 and the closure element 11, as illustrated in FIG. 1, is an example of a liquid-tight connection and protects the abdominal wall 4 and the incision safely from contamination.

Figure 2:
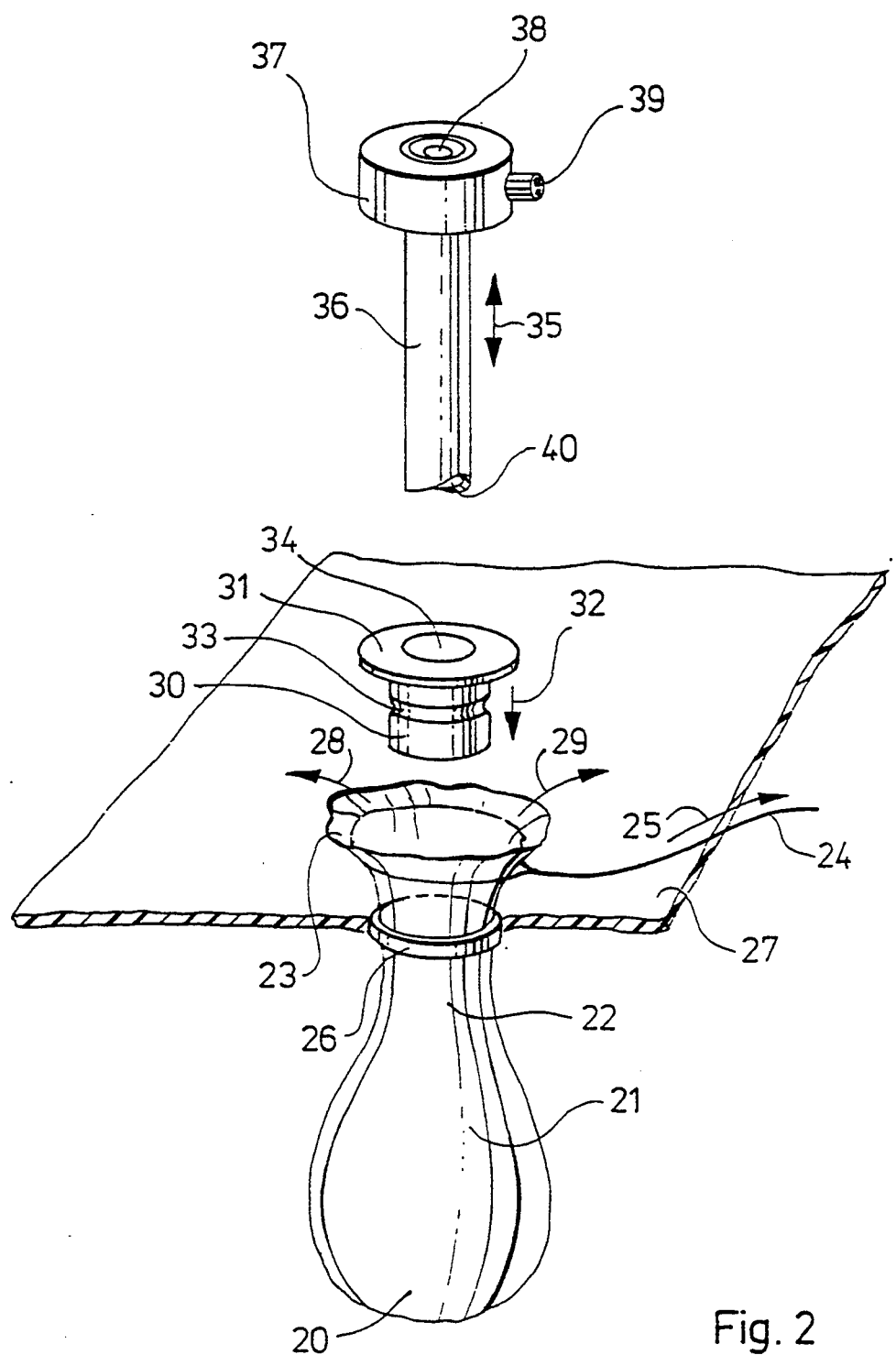
FIG. 2 shows an exploded view of the accessory device according to the invention.

FIG. 2 is an exploded view showing elements of the invention. The illustration shows the plastic receptacle 20 in its open condition. The figure does not show the relation between the different elements and the abdominal wall. A plastic receptacle 20 is made from a transparent flexible material. In addition, fibers may be incorporated in the material for the purpose of increasing its tearing strength.

The figure shows the flexible and foldable plastic receptacle 20 in its unfolded condition. The receptacle is composed of a spherical section 21 and a cylindrical section 22. In the area of the free end 23, a cord 24 is integrated in the cylindrical section 22 which, when pulled together in the direction indicated by arrow 25, safely closes the cylindrical section 22.

The cylindrical section 22 of the plastic receptacle 20 is enclosed, at a certain spacing, by a ring 26 which is part of a cover sheet 27. The ring 26 is firmly connected with the cover sheet 27. The material thickness of the ring 26 is greater than that of the cover sheet 27. The free end 23 of the cylindrical section 22 can be expanded in the directions of arrows 28, 29 in such a way that a hollow-cylindrical section 30 of a closure element 31 can be introduced into the cylindrical section 22 of the plastic receptacle 20 in the direction of arrow 32. The closure element 31 is adapted to the ring 26 in such a way that the ring 26 can be detachably locked in position on the hollow-cylindrical section 30 via notches 33. In the locked condition, the cylindrical section 22 of the plastic receptacle 20 is then firmly held against displacement and against movement between the closure element 31 and the ring 26. A hollow-cylindrical tube 36 can be displaced in liquid-tight relationship in the directions of arrow 35 within an opening 34 of the closure element 31. The free end 37 of the tube 36 is provided with an opening 38 which is equipped with a seal. In addition, a tubular connection piece 39 is provided on the free end 37, which communicates with a lumen 40 of the tube 36. The tube 36 serves as shaft for instruments serving for crushing tissue and/or calculi. The connection piece 39 can be used as irrigation and/or suction channel. There is further the possibility to provide an additional channel on the tube 36 for the purpose of unfolding the plastic receptacle 20 intra-abdominally by application of a higher gas pressure.

Figure 3:
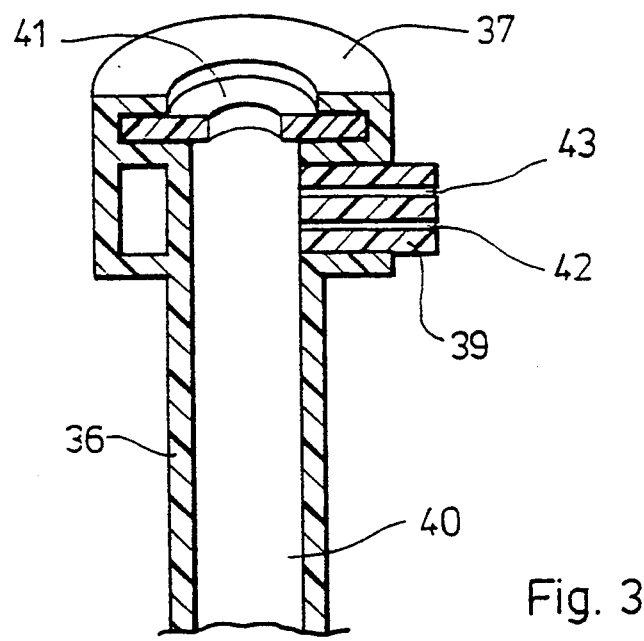
FIG. 3 shows a section through a hollow cylinder of the type that can be introduced into a closure element in sealing relationship.

FIG. 3 shows a sectional view of the tube 36 as described by way of example with reference to FIG. 2. The free end 37 of the tube 36 has a sleeve-like configuration and accommodates a seal 41 serving to seal off the instruments when the latter are introduced. The connection piece 39 is passed by the channels 42, 43. The channels 42, 43 communicate with the lumen 40. The outer diameter of the tube 36 is adapted to the opening of the respective closure element.

Figure 4:
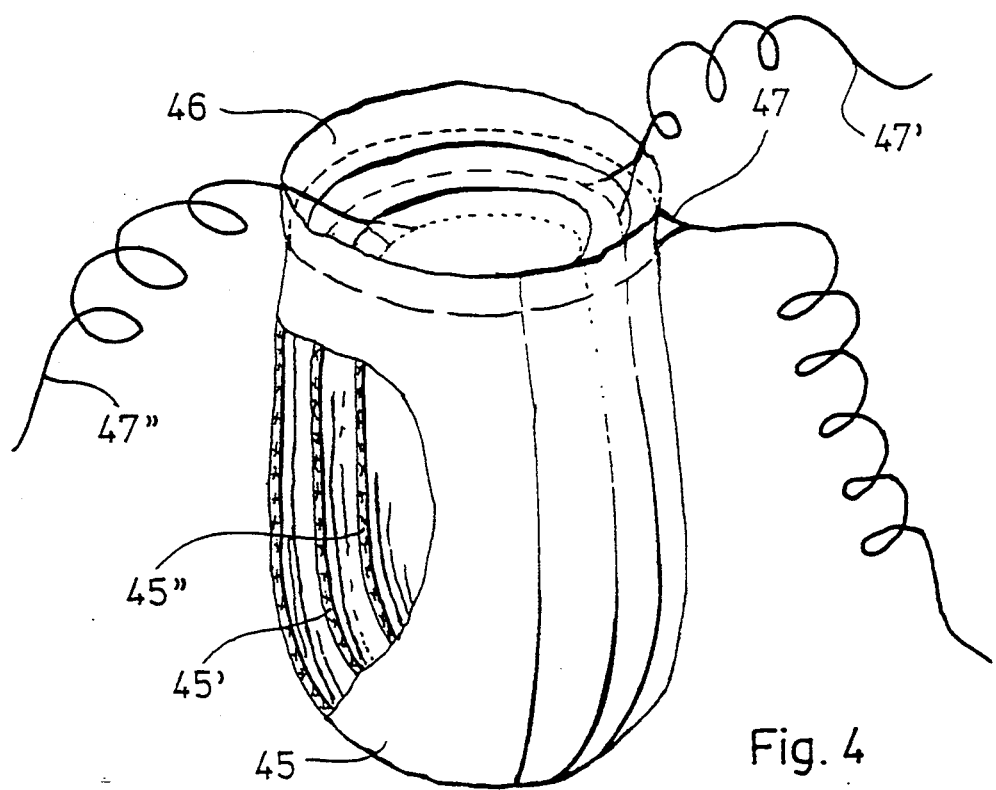
FIG. 4 shows a plastic receptacle according to the invention comprising a plurality of additional plastic receptacles seated in the plastic receptacle.

FIG. 4 shows a very diagrammatic representation of a plastic receptacle 45 according to the invention which in the unfolded state exhibits a substantially cylindrical shape. The plastic receptacle 45 is made from a highly tear-resisting film comprising fiber-reinforced elements. In the area of the opening 46, a cord 47 is integrated in the material of the plastic receptacle 45, by means of which the plastic receptacle 45 can be closed. Inside the plastic receptacle 45, there may be arranged further plastic receptacles 45', 45" as required, which can be removed from the plastic receptacle 45 inside the abdominal space. The cords 47, 47', 47" enable the respective plastic receptacle 45, 45', 45" to be manipulated from one outside.

Figure 5:
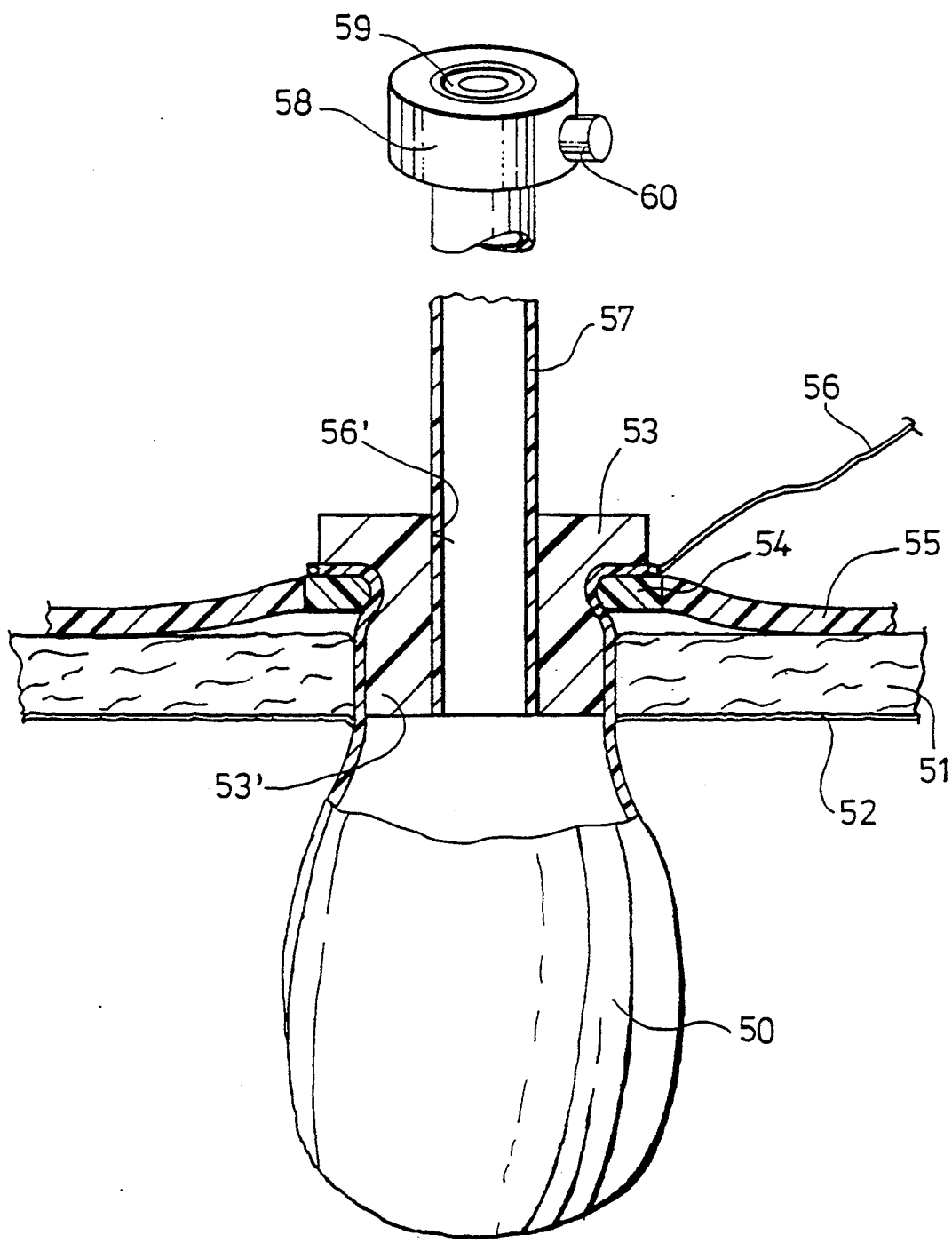
FIG. 5 shows an enlarged sectional view of an accessory device according to the invention, with the closure element extending through the abdominal wall.

FIG. 5 is a—partly sectional—representation of a plastic receptacle 50 in its partly intra-abdominal position. The shaft of the plastic receptacle 50 extends through an abdominal wall 51 and a peritoneum 52. A closure element 53, of flange-like and plug-like design, engages the plastic receptacle 50, has a cylindrical section 53' extending through the abdominal wall 51 and the peritoneum 52, and is in locking engagement with a ring 54 of a cover sheet 55. Reference numeral 56 indicates a cord by means of which the plastic receptacle 50 can be closed and reopened in the manner of a tobacco pouch. Due to the locking engagement between the closure element 53 and the ring 54, the plastic receptacle 50 is secured to the cover sheet 55 in sealing relationship and free from displacement. An opening 56' in the closure element 53 is adapted to sealingly receive a hollow cylinder 57 whose free end is provided with a sleeve 58 which is suited to hold crushing tools in sealing relationship and to guide them in the hollow cylinder 57 in stable position. A seal is indicated in the figure by reference numeral 59. The seal 59 sealingly encloses, for example, a lithotripsy device so that the hollow cylinder 57 and the inner volume of the plastic receptacle 50 can be filled with gas and/or irrigated via a connection piece 60. The connection piece 60 also can be used for extraction purposes, or for introducing a gas for unfolding the plastic receptacle 50 in its position inside the abdominal space.

As can be seen in FIG. 5, the closure element 53 extends through the abdominal wall and urges the outer wall of the plastic receptacle 50 in sealing relationship against the inner circumferential surface of the umbilical incision. The pneumoperitoneum is preserved.

We claim:

1. An accessory device for laparoscopic operations comprising: a cover sheet with an integrated ring having an opening; a first flexible and folded plastic receptacle having a shaft and an end, the shaft being located within the ring opening; a closure element adapted to couple together the shaft and the ring in sealing relationship; and a plurality of additional plastic receptacles nested within another and within the first plastic receptacle.

2. An accessory device according to claim 1, wherein the end extends through the ring, and the shaft is immovably held in looking engagement between the ring and the closure element.

3. An accessory device according to claim 1, wherein, the plastic receptacle is made from a transparent material.

4. An accessory device according to claim 3, wherein, in an unfolded state; the plastic receptacle comprises a spherical section and a cylindrical section.

5. An accessory device according to claim 1 wherein the cover sheet is made from a material compatible with human skin.

6. An accessory device for laparoscopic operations comprising: a covet sheet with an integrated ring having an opening; a first flexible and foldable plastic receptacle having a shaft and an end, the shaft being located within the ring opening; a closure element adapted to couple together the shaft and the ring in sealing relationship, and a cord, having an easily distinguishable color, integrated with the receptacle, the cord being shaped as a loop and the end and the cord being configured to cooperate such that pulling the loop together closes the respectable.

7. An accessory device according to claim 6, wherein the end extends through the ring, and the shaft is immovably held in locking engagement between the ring and the closure element.

8. An accessory device according to claim 6, wherein the plastic receptacle is made from a transparent material.

9. An accessory device according to claim 8, wherein, in an unfolded state, the plastic receptacle comprises a spherical section and a cylindrical section.

10. An accessory device according to claim 6 wherein the cover sheet is made from a material compatible with human skin.

11. An accessory device for laparoscopic operations through a patient's abdominal wall comprising: a cover sheet with an integrated ring having an opening; a first flexible and foldable plastic receptacle having a shaft and an end, the shaft being located within the ring opening; and a closure element adapted to couple together the shaft and the ring in sealing relationship, the closure element being provided with a cylindrical section having an annular groove formed on its outer circumferential surface, the section also having an opening, and a diameter and a length, the diameter and length being adapted to extend through the abdominal wall and the section opening being adapted to engage an outer diameter of a hollow cylinder in form-locking and sealing relationship, the follow cylinder having a free end, a lumen, a sealable opening at the free end, and a plurality of tubular connection pieces adapted to communicate with the lumen, and wherein the ring is adapted to be brought into locking engagement with the annular groove.

* * * * *